Jan. 5, 1960 H. C. SWIM Plant Pat. 1,894
ROSE PLANT
Filed April 2, 1959
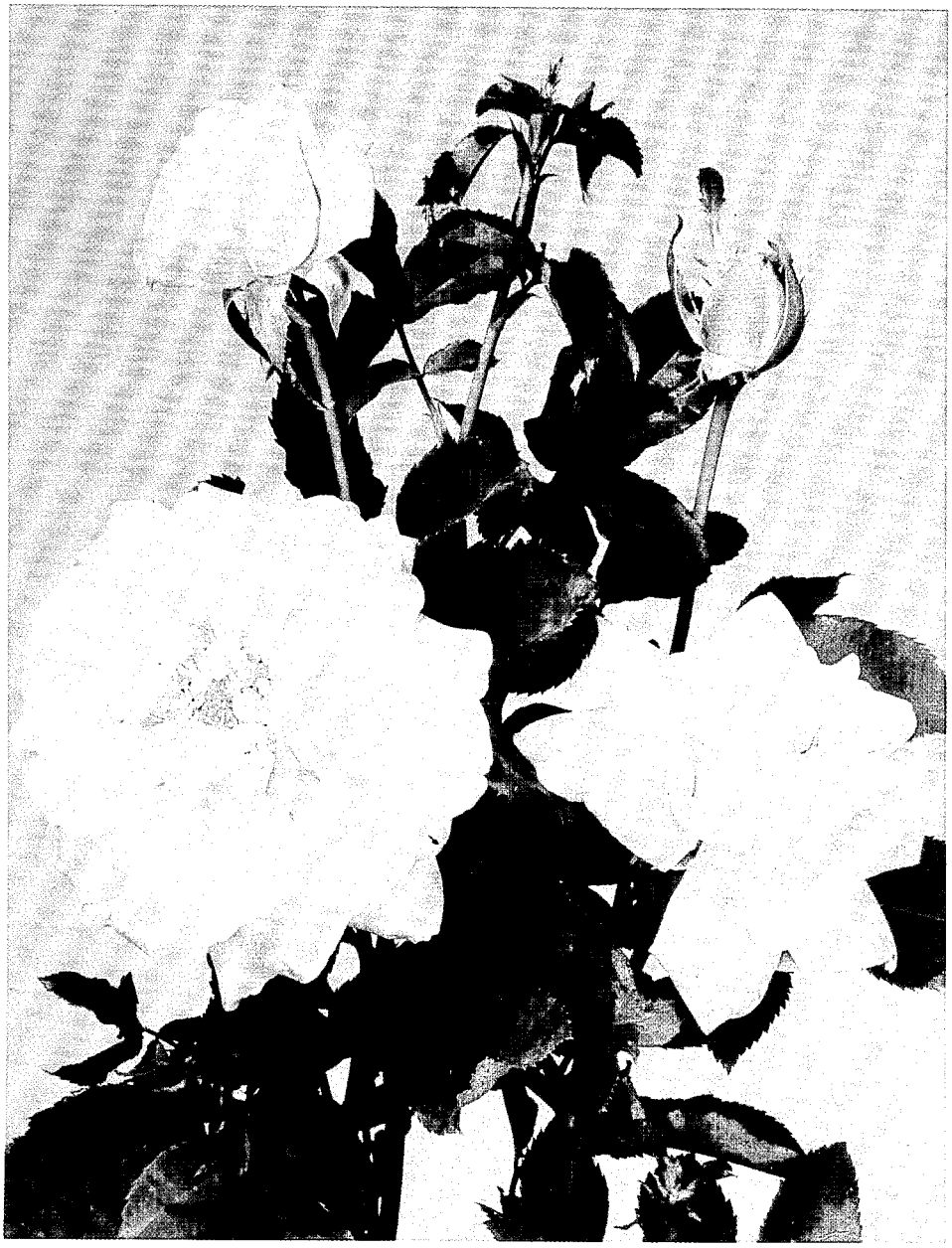
Inventor.
H. C. Swim
By: Robb & Robb
Attorneys.

United States Patent Office

Plant Pat. 1,894
Patented Jan. 5, 1960

1,894

ROSE PLANT

Herbert C. Swim, Ontario, Calif., assignor to Armstrong Nurseries, Inc., Ontario, Calif., a corporation of California Application April 2, 1959, Serial No. 803,813

1 Claim. (Cl. 47—61)

The present invention relates to a new and distinct variety of rose plant of the hybrid tea class, which was originated by me by crossing the variey "Charlotte Armstrong" (Plant Patent No. 455) with the variety "Girona" (unpatented), the latter variety being a hybrid tea rose which bears large, well-formed double flowers of a blend of red and yellow, which have a strong fragrance and are borne on relatively long, single stems.

The general objective of this breeding was to produce improved varieties of the hybrid tea type having flowers which fall in the yellow-to-red color range, and any combination of these colors, while maintaining the good form, size and fragrance of the flowers of the parent varieties. This objective has been achieved in the new variety which is the subject hereof, as evidenced by the following unique combination of characteristics which are outstanding in the new variety and which distinguish it from its parents as well as from all other varieties of which I am aware:

(1) A vigorous, upright-spreading plant habit;

(2) Attractive dark yellow-green foliage of a size ranging from medium to large;

(3) A floriferous habit, with the flowers usually borne singly, but sometimes in small clusters, and on stems ranging from medium length to long;

(4) Attractive, large, double, well-formed flowers of long-lasting quality; and (5) A generally light to medium yellow general color tonality of the blooms.

In comparison with its seed parent, "Charlotte Armstrong," the new variety has a shorter and more compact flower bud form, as distinguished from the long, urn-shaped buds of the parent variety, and the flower color of the new variety generally ranges from light to medium yellow, as distinguished from the dark pink or light cerise color of the blooms of "Charlotte Armstrong."

As compared with the pollen parent, "Girona," the new variety has a more branched habit of growth and bears more flowers on somewhat shorter stems; the flower fragrance ranges from slight to moderate, as distinguished from the strong and penetrating fragrance of the flowers of "Girona," and the flower color generally ranges from light to medium yellow, whereas that of "Girona" is a blend of red and yellow.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Charlotte Armstrong."

*Pollen parent.*—"Girona."

Propagation: Holds its distinguishing characteristics through succeeding propagations by budding.

*Flower*

Locality where grown and observed: Ontario, California.

Flowers borne: Usually singly, but sometimes from to five to stem; in irregular clusters; on strong stems ranging from medium length to long.

Quantity of bloom: Abundant, outdoors.

Continuity: Nearly continous during growing season.

Fragrance: From slight to moderate.

Bud:

*Peduncle.*—From average length to long; from average caliper to heavy; erect; usually smooth; with few hairs. Color—near Deep Chrysolite Green, Plate XXXI (Ridgway).

*Before calyx breaks.*—Size—medium. Form—medium length; ovoid.

*As calyx breaks.*—Color—markings of between Spinel Red, Plate 0023, page 189 (Wilson) and Erythrite Red, Plate 0027, page 190 (Wilson) where first exposed, blending into near Mars Orange, Plate 013/2, page 104 (Wilson); all overlaying a ground color of near Indian Yellow, Plate 6/2, page 6 (Wilson) where last sepals unfold.

*Sepals.*—Margins of alternate sepals usually lined with few to several stipitate glands and none to few slender foliaceous parts; margins of other sepals lined with fine, woolly tomentum; foliaceous appendages sometimes extend beyond tip equal to ⅓ or more of sepal length. Inner surface—with fine, woolly tomentum. Outer surface — usually smooth.

*As first petal opens.*—Size—average. Form—medium length; from ovoid to urn-shaped. Color; outside—between Indian Yellow, Plate 6/2, page 6 (Wilson) and Cadmium Orange, Plate 8/2, page 8 (Wilson); some markings and shadings of between Vermilion, Plate 18/2, page 18 (Wilson) and Geranium Lake, Plate 20/2, page 20 (Wilson); with small area at base near Aureolin, Plate 3/1, page 3 (Wilson); inside—between Indian Yellow, Plate 6/2, page 6 (Wilson) and Cadmium Orange, Plate 8/3, page 8 (Wilson); some markings and shadings of between Vermilion, Plate 18/3, page 18 (Wilson) and Geranium Lake, Plate 20/3, page 20 (Wilson); with area at base of petal near Aureolin, Plate 3, page 3 (Wilson).

*Opening.*—Opens up well; is not retarded from opening by cold, hot, wet or dry weather.

Bloom:

*Size (when fully open).*—From average to large; from 3½ inches to 5 inches.

*Petalage.*—Double; from 25 to 35 petals, plus from 8 to 10 petaloids; arranged regularly.

*Form.*—High-centered at first, but becoming cupped to high-centered; petals being at first somewhat tightly cupped, with tips reflexed, but becoming later at maturity more loosely flat to cupped, with tips reflexed; lateral margins of petals of newly opened flower usually reflexed ⅓ or more of petal length; apex of petals of newly opened flower usually reflexed ⅓ or more of petal length.

Petals:

*Texture.*—Moderately leathery. Inside—from satiny to velvety. Outside—satiny.

*Shape.*—Outer—broadly obovate, with apex flat; usually with 1 or 2 notches. Intermediate—obovate, with apex from rounded to flat; with 1 or 2 notches. Inner—narrowly obovate, with apex rounded.

This description of a newly opened flower was made from a rose grown outdoors in the month of October, at Ontario, California:

*Color.*—Outer petal: outside surface—between Indian Yellow, Plate 6/3, page 6 (Wilson) and Cadmium Orange, Plate 8/3, page 8 (Wilson); some markings and shadings of between Vermilion, Plate 18/2, page 18 (Wilson) and Carmine, Plate 21/2, page 21 (Wilson); with small area at base near Aureolin, Plate 3/1, page 3 (Wilson); inside surface—between Indian Yellow, Plate 6/3, page 6 (Wilson) and Cadmium Orange, Plate 8/2, page 8 (Wilson); some markings and shadings of between Vermilion, Plate 18/3, page 18 (Wilson) and Carmine, Plate 21/3, page 21 (Wilson); with small area at base near Aureolin, Plate 3, page 3 (Wilson). Intermediate petal: outside surface—near Canary Yellow, Plate 2/3, page 2 (Wilson); with small area at base near Aureolin, Plate 3/1, page 3 (Wilson); inside surface—near Lemon Yellow, Plate 4/3, page 4 (Wilson); occasional petal has streak from base to apex near Geranium Lake, Plate 20/3, page 20 (Wilson); with small area at base near Aureolin, Plate 3, page 3 (Wilson). Inner petal: outside surface—near Canary Yellow, Plate 2/3, page 2 (Wilson); with small area at base near Aureolin, Plate 3/1, page 3 (Wilson); inside surface—near Aureolin, Plate 3/2, page 3 (Wilson); occasional petal has small streaks from base to apex near Geranium Lake, Plate 20/2, page 20 (Wilson); with small area at base near Aureolin, Plate 3, page 3 (Wilson).

This description was made from a rose that was open for 3 days outdoors in the month of October at Ontario, California:

*Color.*—Outer petal: outside surface—near Straw Yellow, Plate 604/3, page 67 (Wilson), blending with near Aureolin, Plate 3/2, page 3 (Wilson) toward base; inside surface—near Straw Yellow, Plate 604/1, page 67 (Wilson), shaded toward margins with near Shrimp Red, Plate 616/3, page 73 (Wilson); with small area at base near Aureolin, Plate 3/2, page 3 (Wilson). Inner petal: outside surface—between Empire Yellow, Plate, 603/3, page 66 (Wilson) and Straw Yellow, Plate 604/3, page 67 (Wilson), usually blending with near Aureolin, Plate 3/2, page 3 (Wilson) toward base; inside surface—near Maize Yellow, Plate 607/3, page 69 (Wilson), blending with near Aureolin, Plate 3/2, page 3 (Wilson) toward base; occasional petal has streaks of near Scarlet, Plate 19/2, page 19 (Wilson) from base toward apex.

*General color effect.*—Newly opened flower—between Lemon Yellow, Plate 4/2, page 4 (Wilson) and Indian Yellow, Plate 6/3, page 6 (Wilson). 3-days open—between Straw Yellow, Plate 604/2, page 67 (Wilson) and Maize Yellow, Plate 607/3, page 69 (Wilson).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—4 or 5 days in November.

*Reproductive organs*

Stamens: Average number; arranged regularly about pistils; a few mixed with petaloids.

Filaments: From medium length to long; from 6 mm. to 15 mm. in length; most with anthers. Color—near Buttercup Yellow, Plate 5/2, page 5 (Wilson).

Anthers: Medium size; all open approximately at once. Color: upper side—margins near Orpiment Orange, Plate 10/2, page 10 (Wilson); remainder near Lemon Yellow, Plate 4/1, page 4 (Wilson); under side—margins near Orpiment Orange, Plate 10/2, page 10 (Wilson); remainder near Lemon Yellow, Plate 4/1, page 4 (Wilson).

Pollen: From moderate to abundant. Color—near Saffron Yellow, Plate 7/1, page 7 (Wilson).

Pistils: Average number; approximately 70 in number.

Styles: Moderately even; average length; from 5 mm. to 10 mm. in length; average caliper; bunched; columnar. Color—upper one-half of style near Vermilion, Plate 18/3, page 18 (Wilson); remainder near Dresden Yellow, Plate 64/3, page 64 (Wilson).

Stigma: Color—near Maize Yellow, Plate 607/1, page 69 (Wilson).

Ovaries: Usually all enclosed in calyx.

Hips: Average length; globular; smooth; walls thick and fleshy. Color (half-mature)—near Calliste Green, Plate VI (Ridgway), overlaid with near Olive Yellow, Plate XXX (Ridgway) on side exposed to sun.

Sepals: Falling soon; medium length; spear-shaped; recurved. Color: inside—near Light Grape Green, Plate XLI (Ridgway); outside—near Biscay Green, Plate XVII (Ridgway).

Seeds: From few to average number; from 2 to 10 in number; usually medium size.

*Plant*

Foliage:

*Leaves.*—Compound of usually from 3 to 7 leaflets; from normal abundance to abundant; from medium size to large; leathery and semi-glossy.

*Leaflets.*—Shape—oval, with apex acute. Base—round. Margin—simply serrate.

*Color.*—Mature: upper surface—between Cress Green, Plate XXXI (Ridgway) and Dark Dull Yellow Green, Plate XXXII (Ridgway); under surface—near Asphodel Green, Plate XLI (Ridgway). Young: upper surface—near Olive, Plate XXX (Ridgway), overlaid with some near Mineral Red, Plate XXVII (Ridgway); under surface—between Army Brown, Plate XL (Ridgway) and Buffy Brown, Plate XL (Ridgway), overlaid with some near Mineral Red, Plate XXVII (Ridgway).

*Rachis (the supporting stem of the compound leaf).*—Average size. Upper side—grooved; with some stipitate glands on edges. Under side—smooth; with from none to 5 or 6 small prickles.

*Stipules.*—Medium length; medium width; with moderately short points turning out at an angle of less than 45°.

*Disease resistance.*—Better than average resistance to mildew, as compared with other varieties grown under comparable cultural conditions at Ontario, California.

Growth:

*Habit.*—Bushy; upright-spreading; much-branched.

*Growth.*—Vigorous.

*Canes.*—From medium caliper to heavy.

*Main stems.*—Color—between Mignonette Green, Plate XXXI (Ridgway) and Rainette Green, Plate XXXI (Ridgway). Large prickles—several; from medium length to long; hooked slightly downward; with medium length, narrow base; color—near Rood's Brown, Plate XXVIII (Ridgway). Small prickles—few; color—near Rood's Brown, Plate XXVIII (Ridgway). Hairs—none.

*Branches.*—Color—near Parrot Green, Plate VI (Ridgway). Large prickles—several; from medium length to long; hooked slightly downward; with medium length, narrow base; color—near Russet, Plate XV (Ridgway). Small prickles—few; color—near Russet, Plate XV (Ridgway). Hairs—none.

*New shoots.*—Color—near Courge Green, Plate XVII (Ridgway), overlaid with near Ecru-Olive, Plate XXX (Ridgway) on side exposed to sun. Large prickles—several; medium length; hooked slightly downward; with medium length, narrow base; color—near Mineral Red, Plate XXVII (Ridgway). Small prickles—few; color—near Mineral Red, Plate XXVII (Ridgway). Hairs—none.

I claim:

A new and distinct variety of rose plant of the hybrid tea class, substantially as herein shown and described, characterized particularly as to novelty by its unique combination of a vigorous, upright-spreading plant habit, attractive dark yellow-green foliage of a size ranging from medium to large, a floriferous habit, with the flowers usually borne singly, but sometimes in small clusters, and on stems ranging from medium length to long, attractive, large, double, well-formed flowers of long-lasting quality, and a generally light to medium yellow general color tonality of the blooms.

No references cited.